(12) United States Patent
Fukuta et al.

(10) Patent No.: US 7,479,132 B2
(45) Date of Patent: Jan. 20, 2009

(54) PATCH MATERIAL FOR IONIC MEDICINE ADMINISTRATION

(75) Inventors: Kenji Fukuta, Yamaguchi (JP); Kanji Sakata, Yamaguchi (JP)

(73) Assignee: Tokuyama Corporation, Shunan-Shi, Yamaguchi (JP)

( * ) Notice: Subject to any disclaimer, the term of this patent is extended or adjusted under 35 U.S.C. 154(b) by 155 days.

(21) Appl. No.: 10/547,920

(22) PCT Filed: Mar. 9, 2004

(86) PCT No.: PCT/JP2004/003029

§ 371 (c)(1),
(2), (4) Date: Sep. 8, 2005

(87) PCT Pub. No.: WO2004/080441

PCT Pub. Date: Sep. 23, 2004

(65) Prior Publication Data

US 2006/0198879 A1  Sep. 7, 2006

(30) Foreign Application Priority Data

Mar. 10, 2003  (JP) ............................ 2003-062726

(51) Int. Cl.
*A61M 31/00* (2006.01)
*A61N 1/30* (2006.01)
*A61K 9/00* (2006.01)
*A61F 13/00* (2006.01)

(52) U.S. Cl. .................. 604/501; 604/20; 424/400; 424/449

(58) Field of Classification Search .................. 604/501, 604/20; 424/400, 449
See application file for complete search history.

(56) References Cited

U.S. PATENT DOCUMENTS

| | | | | |
|---|---|---|---|---|
| 3,875,937 A | * | 4/1975 | Schmitt et al. | 604/307 |
| 5,125,894 A | * | 6/1992 | Phipps et al. | 604/20 |
| 6,743,432 B1 | * | 6/2004 | Yanai et al. | 424/400 |

FOREIGN PATENT DOCUMENTS

| | | |
|---|---|---|
| JP | 03-094771 | 4/1991 |
| JP | 04-297277 | 10/1992 |
| JP | 2000-229128 | 8/2000 |
| JP | 2002-338721 | 11/2002 |
| WO | WO 90/04433 | 5/1990 |
| WO | WO 97/23206 | 7/1997 |

* cited by examiner

*Primary Examiner*—Jacqueline F. Stephens
(74) *Attorney, Agent, or Firm*—Norris, McLaughlin & Marcus; Bruce S. Londa (57) ABSTRACT

The present invention discloses a patch for use in administration of an ionic medicine into a living body by infiltration of the ionic medicine into the living body through the living body surface without voltage application, characterized in that the patch comprises an ion-exchange membrane having a surface roughness (Rz) of 7 μm or less at its part to be brought into contact with the living body surface and an ionic medicine impregnated into the ion-exchange membrane.

10 Claims, 1 Drawing Sheet

PATCH MATERIAL FOR IONIC MEDICINE ADMINISTRATION

TECHNICAL FIELD

The present invention relates to a patch used in transdermal administration of an ionic medicine. The patch enables infiltration of an ionic medicine into a living body without voltage application.

BACKGROUND ART

As the method for medicine administration into human or other living bodies, methods by oral administration or injection are known widely. As an administration method coming next to them, a method by transdermal administration is drawing attention. The transdermal administration method enables painless administration of a medicine to an intended affected part over a long period of time. Further, the transdermal patch used in the transdermal administration method has various advantages such as small size, easy carrying and the like. Hence, development of various transdermal patch has been made in recent years.

These transdermal patchs have a medicine layer wherein a medicine solution is impregnated into a medicine-holding material such as hydrophilic polymer, cotton cloth or the like. In using such a transdermal patch, the medicine layer is allowed to make tight contact with the skin of living body. Thereby, the medicine is infiltrated into the living body through the skin.

In this administration method, the concentration difference of medicine acts as a driving force and the medicine is infiltrated into the living body, in general. However, since the infiltration rate of ordinary medicine into living body surface (e.g. skin or mucous membrane) is small, there is a problem that it is impossible to administer a large amount of a medicine into a living body at once. In order to increase the efficiency of medicine administration, it is conducted to enhance the medicine concentration in the transdermal patch used. In this approach, however, it is necessary to impregnate a medicine (which is expensive) into a medicine layer in an amount more than required in administration; consequently, the amount of medicine exceeding the amount required in administration becomes useless. Further, the medicine is administered into the living body in a solution state; therefore, when the solubility of medicine is low, there is a problem that it is impossible to obtain the medicine solution in a required amount.

As the method for alleviating these drawbacks in the transdermal administration of ionic medicine, there is known an iontophoresis method which comprises infiltrating a medicine ion into a living body by electrophoresis. Further, in order to increase the amount of medicine to be administered, there are proposals on a new iontophoresis method which comprises infiltrating a medicine ion into a living body through an ion-exchange membrane placed on the surface of a living body (JP 1991-94771A, National Publication of International Patent Application No. 1991-504343, JP 1992-297277A, JP 2000-229128A). The ion-exchange membranes used in these proposals are commercial products using, as the base material, a woven cloth, which is used in salt manufacture or dialysis of food compounds.

In the iontophoresis, an apparatus of complicated structure provided with electrodes for voltage application and an electric source is needed in administration of a medicine. Accordingly, the iontophoresis using an ion-exchange membrane is inferior in portability and small size which are the important merits of transdermal administration method and, moreover, has a problem that the apparatus used therein is inevitably expensive.

DISCLOSURE OF THE INVENTION

The present inventors made a study in order to solve the above-mentioned problems. As a result, it was found that the amount of the intended medicine administered can be increased significantly without voltage application, by administering a medicine transdermally in a state that an ion-exchange membrane having a smooth surface has been tightly contacted with the surface of a living body. The present invention has been completed based on this finding. Accordingly, the present invention aims at providing a patch material used in administration of an ionic medicine, which has a portable and simple structure and which can transdermally administer an ionic medicine in an increased amount.

The present invention is shown below.

[1] A patch for use in administration of an ionic medicine into a living body by infiltration of the ionic medicine into the living body through the living body surface without voltage application, characterized in that the patch comprises an ion-exchange membrane having a surface roughness (Rz) of 7 μm or less at its part to be brought into contact with the living body surface and an ionic medicine impregnated into the ion-exchange membrane.

[2] The patch according to [1], wherein the ion-exchange membrane comprises a porous membrane made of a thermoplastic resin as the base material and an ion-exchange resin contained in voids of the base material.

[3] The patch according to [2], wherein the ion exchange resin is a crosslinked ion exchange resin.

[4] The patch according to [1], wherein an adhesive layer has been formed along the periphery of the part of the ion-exchange membrane to be brought into contact with the living body surface.

[5] A patch for use in administration of an ionic medicine into a living body by infiltration of the ionic medicine into the living body through the living body surface without voltage application, characterized in that the patch comprises an ion-exchange membrane having a surface roughness (Rz) of 7 μm or less at its part to be brought into contact with the living body surface, an ionic medicine impregnated into the ion-exchange membrane, and an ionic medicine-containing layer formed on the side of the ion-exchange membrane opposite to its side having the part to be brought into contact with the living body surface.

[6] The patch according to [5], wherein the ion-exchange membrane comprises a porous membrane made of a thermoplastic resin as the base material and an ion-exchange resin contained in voids of the base material.

[7] The patch according to [6], wherein the ion-exchange resin is a crosslinked ion-exchange resin.

[8] The patch according to [5], wherein a pressure-sensitive adhesive layer has been formed along the periphery of the part of the ion-exchange membrane to be brought into contact with the living body surface.

In the patch for administration of ionic medicine, of the present invention, an ion-exchange membrane is contacted tightly with the surface of a living body, whereby an ionic medicine can be administered in a large amount as compared with when conventional patches are used. The details of the action mechanism of the present patch is unknown; however, it is presumed that the medicine is locally concentrated in the ion exchange membrane owing to the ion-exchange action, thereby the concentration difference of medicine between membrane inside and living body inside, resultantly a higher administration amount is achieved.

Such a higher administration amount is achieved only when there is used an ion-exchange membrane having a surface roughness of 7 μm or less. This ion-exchange membrane can be easily produced by using a porous membrane as the base material. It is presumed that the ion-exchange membrane using a porous membrane as the base material, as compared with an ion-exchange membrane using a woven cloth as the base material, has a smooth surface and accordingly has tighter contact with the surface of a living body, and can achieve a larger administration amount.

The patch of the present invention for administration of an ionic medicine using an ion-exchange membrane of 7 μm or less in surface roughness has various advantages possessed by the transdermal administration method of medicine and further enables an extremely large administration amount of medicine which has been unachievable with conventional transdermal administration methods. Therefore, the patch of the present invention exhibits very excellent effects in all applications where the transdermal administration of medicine has been considered, including beauty application, medical application, health promotion application (where a supplement is administered) and the like, and can be used suitably in such applications.

BRIEF DESCRIPTION OF THE DRAWINGS

In the drawings, 1 is a living body surface; 2 is an ion-exchange membrane; 3 is an ionic medicine-containing layer; 4 is a sheathing material; 5 is a bonded area; 6 is a periphery; 20 is a virtual skin or a living body skin; 21 is a to-be-examined membrane; 22 is a medicine solution chamber; 23 is a virtual skin chamber; and 100 is a patch material.

BEST MODE FOR CARRYING OUT THE INVENTION

The patch of the present invention comprises an ion-exchange membrane having a surface roughness (Rz) of 7 μm or less at its part to be brought into contact with the surface of a living body and an ionic medicine impregnated into the ion-exchange membrane. The present patch may comprise as necessary an ionic medicine-containing layer formed on the side of the ion-exchange membrane opposite to its side having the part to be brought into contact with the living body surface. Or, the present patch may equip a member which functions so as to prevent, for example, leakage of the ionic medicine outside from the patch. The ionic medicine may be present in the patch as it is or in its solution dissolved in a solvent such as water, alcohol or the like.

The present patch is used in order to administer an ionic medicine useful to a living body, into the living body transdermally and not by oral administration or by injection.

The ionic medicine comprises a positive ion and a negative ion. As the ionic medicine, any ionic medicine may be used with no particular restriction as long as its positive ion or negative ion is administered into a living body and exhibits a pharmacological effect.

As the ionic medicine whose positive ion exhibits a pharmacological effect, there can be mentioned, for example, anesthetics such as procaine hydrochloride, lidocaine hydrochloride, dibucaine hydrochloride and the like; anti-malignant tumor agents such as mitomycin, bleomycin hydrochloride and the like; analgesics such as morphine hydrochloride and the like; steroids such as medroxyprogesterone acetate and the like; and histamine.

As the ionic medicine whose negative ion exhibits a pharmacological effect, there can be mentioned vitamin agents such as vitamin B2, vitamin B12, vitamin C, vitamin E, folic acid and the like; anti-inflammatory agents such as aspirin, ibuprofen and the like; adrenocortical hormones such as dexamethasone-based water-soluble agent and the like; antibiotics such as benzylpenicillin potassium and the like; insulin; and so forth.

In the present patch, such an ionic medicine is impregnated into an ion-exchange membrane.

Of the surface of the ion-exchange membrane, the part to be brought into contact with the surface of a living body has a surface roughness (Rz) of 7 μm or less. With a patch produced using an ion-exchange membrane having a surface roughness exceeding 7 μm or a porous membrane having no ion-exchange group, there is substantially no infiltration of an ionic medicine into a living body unless voltage application is made. In other words, by using an ion-exchange membrane having a surface roughness of 7 μm or less, there is infiltration of an ionic medicine into a living body without voltage application.

There is not made clear the reason why infiltration of an ionic medicine into a living body occurs without voltage application, unlike when there is used a conventional medicine-administration apparatus (an apparatus for iontophoresis) which can infiltrate a medicine into a living body by voltage application. The present inventors presume that the reason is that, with an ion-exchange membrane having a small surface roughness, i.e. a smooth surface, the effective contact area between ion-exchange membrane and living body surface becomes extremely large.

Incidentally, the surface roughness (Rz) is a 10-point height of roughness profile specified by JIS B 0601-1994.

As the ion-exchange membrane used in the present invention, there can be used any known ion-exchange membrane with no particular restriction as long as it has a surface roughness (Rz) of 7 μm or less at its part to be brought into contact with the surface of a living body. The surface roughness (Rz) of the ion-exchange membrane is preferably 5 μm or less, more preferably 3 μm or less, particularly preferably 1 μm or less. In the present ion-exchange membrane, it is sufficient that the surface roughness is in the above range at the part to be contacted with the surface of a living body, and the surface roughness of other surface part has no particular restriction. That is, the surface roughness (Rz) of the surface part other than the part to be contacted with a living body may be larger than 7 μm. [Hereinafter, the ion-exchange membrane having a surface roughness (Rz) of 7 μm or less at its part to be contacted with the surface of a living body may be referred to as "ion-exchange membrane having a surface roughness (Rz) of 7 μm or less" or simply as "ion-exchange membrane".]

The ion-exchange group possessed by the ion-exchange membrane used in the patch of the present invention is selected depending upon the electric charge of the ionic medicine to be administered. There is used a membrane which exchanges an ion of the same electric charge as the electric charge of the pharmacologically effective ion of the ionic medicine to be administered. That is, when the pharmacologically effective ion of the medicine to be administered is charged positively, there is used a membrane having a cation-exchange group (a cation-exchange membrane). When the pharmacologically effective ion of the medicine to be administered is charged negatively, there is used a membrane having an anion-exchange group (an anion-exchange membrane).

As the ion-exchange group, there can be used any group with no particular restriction as long as it is a functional group which can be charged negatively or positively in an aqueous solution. As specific examples of the functional group which can become a cation(positive ion)-exchange group, there can be mentioned sulfonic acid group, carboxyl group and phosphonic acid group. In general, sulfonic acid group (which is a strongly acidic group) is preferred particularly.

As the anion(negative ion)-exchange group, there can be mentioned primary to tertiary amino groups, quaternary ammonium group, pyridyl group, imidazole group, quaternary pyridinium group, quaternary imidazolium group, etc. In general, quaternary ammonium group and quaternary pyridinium group (which are both a strongly basic group) are used suitably.

In order to impregnate large amount of ionic medicine possible and resultantly increase the amount of the ionic medicine administered into a living body, the fixed ion concentration of ion-exchange membrane is preferably 0.3 to 15.0 mmol/g-water, more preferably 0.6 to 12.0 mmol/g-water.

An ion-exchange membrane having such a fixed ion concentration can be obtained by controlling the ion-exchange capacity and water content of ion-exchange membrane. The fixed ion concentration of ion-exchange membrane is defined by [ion-exchange capacity/water content]. Therefore, a larger ion-exchange capacity gives a higher fixed ion concentration.

The ion-exchange capacity of ion-exchange membrane is generally larger as the amount of the ion-exchange group introduced into the ion-exchange membrane is larger. In order to obtain an ion-exchange membrane having the above-mentioned fixed ion concentration, the ion-exchange capacity of the membrane is preferably 0.1 to 6.0 mmol/g of dry membrane, particularly preferably 0.3 to 4.0 mmol/g of dry membrane.

Meanwhile, the fixed ion concentration of ion-exchange membrane is higher as the water content of the membrane is lower. However, when the water content is too low, the migration resistance of ionic medicine in ion-exchange membrane is high. Accordingly, the water content in ion-exchange membrane is preferably 5% by mass or more, more preferably 10% by mass or more relative to the dry mass of the ion-exchange membrane.

In general, there is suitably used an ion-exchange membrane having a water content of 5 to 90% by mass, preferably 10 to 50% by mass.

The water content of ion-exchange membrane can be kept in the above range by appropriately selecting the kind of ion-exchange group, ion-exchange capacity, crosslinking degree, etc. of ion-exchange membrane.

The thickness of ion-exchange membrane is preferred to be larger in order to obtain a larger physical strength. Meanwhile, the thickness is preferred to be smaller in order to obtain a better fitness to living body surface. In consideration of these matters, the thickness is preferably 5 to 150 µm, more preferably 10 to 120 µm. An ion-exchange membrane having a thickness in this range can be produced easily.

The ion-exchange membrane can be produced by any method as long as it does not contain any impurity harmful to living body. An ion-exchange membrane obtained by using, as the base material (which is also called a reinforcing material or a supporting material), a porous membrane (e.g. a porous membrane or an unwoven cloth of smooth surface) and impregnating an ion-exchange resin into the voids of the porous membrane, is preferred because such an ion-exchange membrane can easily have a surface roughness of 7 µm or less. By using a porous membrane as a base material, an ion-exchange membrane of smooth surface can be produced far more easily than when a woven cloth is used as a base material. Also, by using a porous membrane as a base material, an ion-exchange membrane can be produced by an extremely easy production method as compared with when no base material is used (e.g. a casting method). Further, by using a porous membrane as a base material, an ion-exchange membrane of high strength can be produced.

The content of the ion exchange resin in the ion-exchange membrane is generally 5 to 95% by mass. The content of the ion exchange resin is preferably 10 to 90% by mass in order to make easy the permeation of medicine ion and further make large the strength of ion-exchange membrane. Incidentally, the content of the ion-exchange resin has a connection also with the voids ratio (described later) of the porous membrane.

Specific Description is made below on the most representative method for production of an ion-exchange membrane using a porous membrane as the base material.

First, into a porous membrane having a smooth surface is impregnated a polymerizable monomer (e.g. styrene) into which an ion-exchange group can be introduced. Then, the surface of the monomer-impregnated porous membrane is covered with a smooth material such as polyester film or the like and, in this state, the impregnated monomer is polymerized. Thereafter, an ion-exchange group is introduced into the polymer (resin) packed in the voids of the porous membrane. Thereby can be produced an ion-exchange membrane used in the present invention.

As to the porous membrane, there is no particular restriction, and any porous membrane can be used as long as it is a film or sheet having a large number of voids (e.g. pores) extending to the both surfaces of the membrane. However, the average pore diameter of the porous membrane is preferably 0.005 to 5.0 µm, more preferably 0.01 to 2.0 µm in order to enable easy production of an ion-exchange membrane having the above-mentioned properties and obtain an ion-exchange membrane of high physical strength. The voids ratio (porosity) of the porous membrane is preferably 20 to 95%, more preferably 30 to 90%. The air permeability (measured by JIS P 8117) of the porous membrane is preferably 1,000 seconds or less, particularly preferably 500 seconds or less.

The thickness of the porous membrane is preferably 5 to 150 µm, more preferably 10 to 120 µm. By using a porous membrane having this thickness, the ion-exchange membrane obtained can have the above-mentioned thickness.

As to the material of the porous membrane, there is no particular restriction and any material can be used. However, the porous membrane is preferred to be made of a thermoplastic resin because, with the thermoplastic resin, production of porous membrane is easy and a bag-shaped patch material (described later) can be easily produced by fusion bonding.

As the thermoplastic resin constituting the porous membrane, there can be used, with no restriction, polyolefin resins, for example, homopolymers or copolymers of α-olefins (e.g. ethylene, propylene, 1-butene, 1-pentene, 1-hexene, 3-methyl-1-butene, 4-methyl-1-pentene and 5-methyl-1-heptene); vinyl chloride-based resins such as polyvinyl chloride, vinyl chloride-vinyl acetate copolymer, vinyl chloride-vinylidene chloride copolymer, vinyl chloride-olefin copolymer and the like; fluoroplastics such as polytetrafluoroethylene, polychlorotrifluoroethylene, polyvinylidene fluoride, tetrafluoroethylene-hexafluoropropylene copolymer, tetrafluoroethylene-perfluoroalkyl vinyl ether copolymer, tetrafluoroethyleneethylene copolymer and the like; polyamide resins such as nylon 6, nylon 66 and the like; polyimide resins; and so forth.

Polyolefin resins are preferred because they are superior in mechanical strength, chemical stability and resistance against chemicals and have good affinity with polystyrene type ion-exchange resins (described later). Of the polyolefin resins, polyethylene and polypropylene are particularly preferred and polyethylene is most preferred.

The porous membrane can be obtained generally by molding a resin composition composed of a thermoplastic resin and an organic liquid, into a sheet or film shape and then extracting the organic liquid from the molding by using a solvent. Or, it can be obtained easily by, for example, stretching a sheet containing an inorganic filler and/or an organic filler. Or, it can be obtained by a method described in, for example, JP 2002-338721A.

It is also possible to use, as the porous membrane, a commercial product, for example, Hipore (a product of Asahi Chemical Co., Ltd.), Upore (a product of Ube Industries, Ltd.), Setela (a product of Tonen Tapirus Co., Ltd.), Expole (a product of Nitto Denko Corporation), or Hilet (a product of Mitsui Chemicals, Inc.).

As to the ion exchange resin contained in the porous membrane, there is no particular restriction, either. As specific examples thereof, there can be mentioned ion exchange resins produced by introducing an ion-exchange group as necessary into a polymer of an aromatic vinyl compound (e.g. styrene, vinylpyridine or vinylimidazole) (the polymer may be hereinafter referred to as polystyrene type resin), or by modifying such a polymer; ion-exchange resins of poly(meth)acrylic acid type; ion-exchange resins made of a perfluorosulfonic acid resin, typified by Nafion (a product of Du Pont); and ion exchange resins obtained by introducing the above-mentioned ion-exchange group into a so-called engineering plastic (e.g. polysulfone, polyethersulfone, polyetherether ketone, polyphenylene oxide or polyimide) or an elastomer [e.g. polystyrene-poly(ethylene-butylene)-polystyrene triblock copolymer].

The ion-exchange resin is preferred to be a crosslinked ion-exchange resin. By using a crosslinked ion-exchange resin, a medicine can be administered at a higher efficiency. A crosslinked ion-exchange resin of polystyrene type is preferred from the standpoints of simple production process, chemical stability, easy introduction of various ion-exchange groups, etc.

The ion-exchange resin of polystyrene type can be produced generally by polymerizing an aromatic vinyl compound into which an ion-exchange group can be introduced, and then introducing an ion-exchange group to the resulting polymer by a known method.

The aromatic vinyl compound into which a cation-exchange group can be introduced, can be exemplified by styrene, α-methylstyrene, 3-methylstyrene, 4-methylstyrene, 2,4-dimethylstyrene, p-tert-butylstyrene, α-halogenated styrene and vinylnaphthalene.

The aromatic vinyl compound into which an anion-exchange group can be introduced, can be exemplified by styrene, vinyltoluene, chloromethylstyrene, vinylpyridine, vinylimidazole, α-methylstyrene and vinylnaphthalene.

The ion-exchange resin is preferred to be a crosslinked type as mentioned above. When a crosslinked ion-exchange resin is produced, a crosslinking monomer is used together in polymerizing an aromatic vinyl compound into which an ion-exchange group can be introduced. As the crosslinking monomer, there can be mentioned, for example, polyfunctional vinyl compounds such as divinylbenzene, divinylsulfone, butadiene, chloroprene, divinylbiphenyl, trivinylbenzene and the like; and polyfunctional methacrylic acid derivatives such as trimethylolmethane trimethacrylic acid ester, methylenebisacrylamide, hexamethylenedimethacrylamide and the like.

The ion-exchange resin may be obtained by adding as necessary, to the monomer into which an ion-exchange group can be introduced and the crosslinking monomer, other hydrocarbon type monomer copolymerizable therewith and a plasticizer and then polymerizing the mixture. As the other monomer, there can be mentioned, for example, acrylonitrile, acrolein and methyl vinyl ketone. As the plasticizer, there can be mentioned, for example, dibutyl phthalate, dioctyl phthalate, dibutyl isophthalate, dibutyl adipate, triethyl citrate, acetyl tributyl citrate and dibutyl sebacate.

As the polymerization initiator used in polymerization of these monomers, there can be used conventional known initiators with no particular restriction. As specific examples of the polymerization initiator, there can be mentioned organic peroxides such as octanoyl peroxide, lauroyl peroxide, tert-butyl peroxy-2-ethylhexanoate, benzoyl peroxide, tert-butyl peroxyisobutyrate, tert-butyl peroxylaurate, tert-hexyl peroxybenzoate, di-tert-butyl peroxide and the like.

In polymerization of the above-mentioned monomers, etc., there may be added known additives ordinarily used in production of an ion-exchange membrane (resin).

As to the proportions of the individual components, it is preferred generally that the monomer into which an ion-exchange group can be introduced, is 100 parts by mass, the crosslinking monomer is 0.1 to 50 parts by mass, preferably 1 to 40 parts by mass and the other monomer copolymerizable with these monomers is 0 to 100 parts by mass.

The proportion of the polymerization initiator added is preferably 0.1 to 20 parts by mass, more preferably 0.5 to 10 parts by mass relative to 100 parts by mass of the monomer into which an ion-exchange group can be introduced.

The polymerization and the introduction of ion-exchange group may be conducted prior to the formation of ion-exchange resin in porous membrane. However, for efficient production of a high-performance ion-exchange membrane, it is preferred to conduct the polymerization and the introduction of ion-exchange group, by impregnating, into the voids of the porous membrane, a monomer composition composed of a monomer into which an ion-exchange group can be introduced, a crosslinking monomer, a polymerization initiator and other components added as necessary (hereinafter, the composition is referred to simply as "monomer composition"), then polymerizing the monomer composition, and introducing, into the resulting polymer, a cation-exchange group or an anion-exchange group.

As to the method for impregnating the monomer composition into the voids of the porous membrane, there is no particular restriction. The impregnation can be conducted, for example, by coating or spraying the monomer composition on the porous membrane or by immersing the porous membrane into the monomer composition. In order to impregnate the monomer composition sufficiently into the voids of the porous membrane, it is possible, for example, to contact the monomer composition with the porous membrane under reduced pressure or, after the contact, to pressurize them.

In polymerizing the monomer composition impregnated into the voids of the porous membrane which becomes a base material, it is preferred to sandwich the monomer composition-impregnated porous membrane between smooth films made of a polyester or the like, and elevating the temperature of the membrane from normal temperature under pressurization of the membrane, to give rise to polymerization. Thereby, the ion-exchange membrane obtained can easily have a surface roughness of 7 μm or less. The pressurization of the porous membrane is made preferably at 0.01 to 1.0 Mpa.

The polymerization conditions may be determined appropriately depending upon the kind of the polymerization initiator used, the formulation of the monomer composition used, etc.

Next, a known ion-exchange group is introduced by using known introduction treatment into the polymer formed in the porous membrane, to obtain an ion-exchange membrane. Introduction of the ion-exchange group may be conducted by appropriately selecting a known method. For example, when a cation-exchange membrane is obtained, there is conducted sulfonation, chlorosulfonation, phosphonium-imparting treatment, hydrolysis or the like. When an anion-exchange membrane is obtained, there is conducted amination, alkylation or the like.

The ion-exchange membrane used in the patch material of the present invention may be an ion-exchange membrane produced by a method other than the method described above, as long as the membrane has a surface roughness of 7 μm or less. Such an ion-exchange membrane can be exemplified by an ion-exchange membrane produced by infiltrating an ion-exchange group-possessing polymer into a porous membrane, and an ion-exchange membrane produced by infiltrating an ion-exchange group-possessing polymerizable monomer into a porous membrane and then polymerizing the polymerizable monomer.

The patch of the present invention comprises at least an ion-exchange membrane having a surface roughness of 7 μm or less and an ionic medicine impregnated into the ion-exchange membrane. As to the method for production of the patch, there is no particular restriction.

As an ordinary production method, there can be mentioned, for example, a method which comprises dissolving an ionic medicine to be impregnated, in a solvent and impregnating the resulting solution into an ion-exchange membrane. As the solvent, water or an alcohol (e.g. ethanol) is preferred. As necessary, the concentration of ionic medicine in ion-exchange membrane may be controlled by, after impregnation of the solution into the ion-exchange membrane, drying the membrane for removal of the solvent therefrom.

As the method for impregnating the ionic medicine into the ion-exchange membrane, there can be mentioned, besides the above-mentioned method of impregnating an ionic medicine into an ion-exchange membrane, a method of, for example, coating or spraying an ionic medicine solution on an ion-exchange membrane.

When an ionic medicine-containing layer (described later) is formed on the ion-exchange membrane, the ionic medicine contained in the layer is fed into the ion-exchange membrane through the interface between the ion-exchange membrane and the ionic medicine-containing layer. Thereby, a patch of the present invention is formed.

The patch of the present invention may comprise only an ion-exchange membrane having a surface roughness of 7 μm or less and an ionic medicine impregnated into the ion-exchange membrane; in other words, the present patch material may be constituted by an ionic medicine-impregnated ion-exchange membrane alone.

However, in order to extend the period of medicine administration, an ionic medicine-containing layer may be formed on a side of the above ion-exchange membrane opposite to its side having a part to be contacted with a living body. In this case, infiltration of ionic medicine into ion-exchange membrane takes place after the production of a patch material during its storage or use even when there is used an ion-exchange membrane containing no ionic medicine, as mentioned previously.

As the ionic medicine-containing layer, there may be used a medicine-containing layer ordinarily used in transdermal administration, with no restriction. That is, the ionic medicine-containing layer can be exemplified by a solution itself, obtained by dissolving an ionic medicine in a solvent such as water, ethanol or the like; and a layer obtained by impregnating this solution into a gel of a polyvinyl alcohol, a polyvinyl pyrrolidone or the like, a porous membrane, a gauze, a paper or the like.

The patch of the present invention may further comprise a solvent-substantially-impermeable sheathing material at the outer surface in order to prevent the ion-exchange membrane or the ionic medicine-containing layer from drying, or an adhesive layer at the periphery in order to increase the adhesivity with the surface of a living body.

As the solvent-substantially-impermeable sheathing material, there is preferred a thermoplastic resin film, particularly a polyolefin type film. By using a thermoplastic film as a sheathing material, the sheathing material can be bonded with the ion-exchange membrane which is made using the previously mentioned thermoplastic resin as the base material, by fusion bonding or the like without using any bonding material such as adhesive or the like. In this case, since no bonding material such as adhesive or the like is used, the incoming of the impurity contained in the adhesive or the like, into the patch material can be prevented.

As to the thickness of the film-shaped sheathing material prepared on the patch, there is no particular restriction. However, the thickness is ordinarily about 5 to 150 μm.

Figure 1:
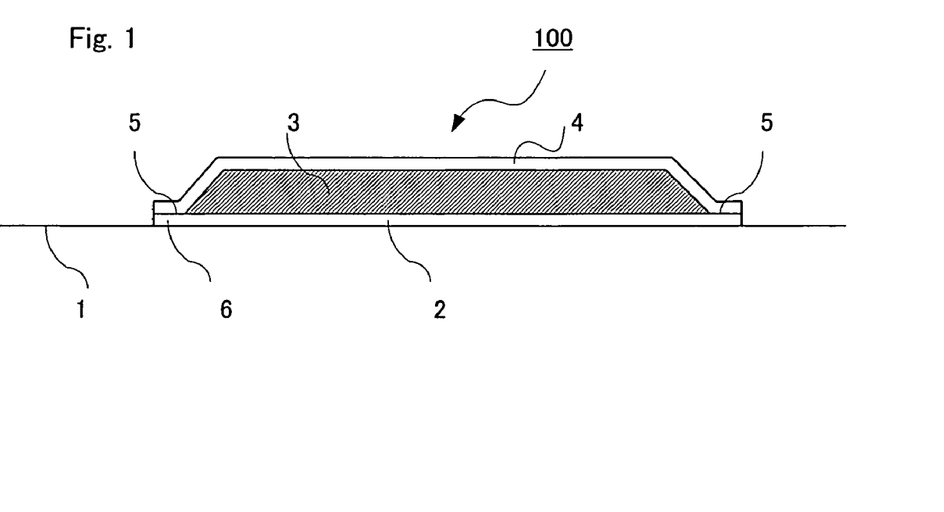
FIG. 1 is a schematic drawing showing a representative structure of the patch of the present invention.

In FIG. 1 is shown a representative structure of a patch having a sheathing material made of, for example, a polyolefin type film. That is, a patch 100 comprises an ion-exchange membrane 2 having a surface roughness of 7 μm or less at the side to be contacted with the surface 1 of a living body and a film-shaped sheathing material 4, and, by bonding of the peripheries 6 of the membrane 2 and the sheathing material 4 with each other, has a bag shape having a closed hollow portion inside. Inside the hollow portion of the bag is put an ionic medicine-containing layer 3. The ion-exchange membrane 2 has therein the same impregnated ionic medicine as the ionic medicine in the ionic medicine-containing layer 3. The film-shaped sheathing material 4 and the ion-exchange membrane 2 are bonded and sealed with each other at their peripheries 6, by fusion bonding or the like.

By attaching the ion-exchange membrane 2 of the patch 100 to the surface 1 of a living body, the ionic medicine infiltrates quickly into the living body from the part of the membrane 2 contacted with the living body.

The film-shaped sheathing material 4 prevents the ionic medicine and other components contained in the ionic medicine-containing layer 3, from vaporization or from attachment to packaging material of patch during storage of patch or to clothes during use of patch.

FIG. 1 is a case where an ionic medicine-containing layer 3 is provided. However, this layer 3 may not be provided, as mentioned previously. Further, the patch may have, for example, an adhesive layer on the side of the patch to be contacted with a living body, at the periphery of the patch material. Furthermore, the patch may have members other than shown in FIG. 1.

There is no particular restriction as to the method for producing the bag-shaped patch 100 shown in FIG. 1. The patch may be produced by any method. For example, an ion-exchange membrane and a film-shaped sheathing material are bonded with each other except each part of their peripheries which is not bonded, whereby is produced a bag which has opening at part of the periphery. Then, an ionic medicine-containing substance is filled inside the bag through the opening of the bag. Then, the opening is bonded to seal the bag. Or, an ionic medicine-containing layer is sandwiched between an ion-exchange membrane and a film-shaped sheathing material and then the peripheries of the ion-exchange membrane and the film-shaped sheathing material are bonded at once for sealing.

As described previously, as the method for bonding and sealing, fusion bonding and sealing is preferred because, with the fusion bonding and sealing, production of patch material is easy, good sealing is kept, and the risk of incoming of impurity into ionic medicine-containing layer is low. There is no particular restriction as to the method for fusion bonding, and any known method used for fusion bonding of a thermoplastic resin-made film can be employed. Ordinarily, fusion bonding is conducted by pushing, against the parts to be bonded, a material which is heatable to a temperature higher by 0 to 100° C. than the melting point of the thermoplastic resin(s) used as the base materials of the sheathing material and the ion-exchange membrane, or by applying, to the parts to be bonded, a vibration of 50 to 300 Hz or a high frequency of 10 to 50 kHz.

For the purpose of, during the period (storage) from production of patch to its use, prevention of leakage of ionic medicine, solvent, etc. to outside of patch or shielding of ionic medicine from harmful environment (oxygen, ultraviolet light, etc.), it is possible to prepare a detachable protective film on the side of the ion-exchange membrane having a part to be contacted with a living body, or to confine the whole patch material in a bag-shaped packaging material.

There is no particular restriction as to the size of the patch of the present invention, and the size may be determined appropriately depending upon the purpose and application of the patch. In general, the diameter or side length is about 0.5 to 50 cm and the thickness is about 40 to 2,300 μm. In this case, the thicknesses of the ion-exchange membrane and the sheathing material used as necessary may be set each at 5 to 150 μm and the thickness of the ionic medicine or the ionic medicine-containing layer may be set at 30 to 2,000 μm. When the above-mentioned film-shaped sheathing material is used, there is no particular restriction as to the size of the periphery at which fusion bonding is made; and the size of the periphery may be set so as to be able to prevent, for example, easy breakage and resultant leakage of the ionic medicine or ionic medicine-containing layer present in the patch material. The width of the periphery may be about 0.1 to 5 mm generally.

The patch of the present invention is used as shown below, ordinarily. That is, the patch is attached to the surface of a living body in such a way that the ion-exchange membrane into which an ionic medicine to be administered has been impregnated, makes tight direct contact with the living body surface [the part of the ion-exchange membrane to be contacted with the living body surface has a surface roughness (Rz) of 7 μm or less]. The attachment of the patch material to the living body surface may also be made through a adhesive layer (mentioned above) formed on the patch. The attachment may also be made by using, for example, a medical adhesive plaster. The place, time length, etc. of the attachment are determined appropriately depending upon, for example, the kind, concentration and desired administration amount of the ionic medicine used.

EXAMPLES

The present invention is described specifically below by way of Examples and Comparative Examples. However, the present invention is not restricted to these Examples. Incidentally, the properties of the ion-exchange membranes shown in Examples and Comparative Examples were measured by the following methods.
(1) Ion-Exchange Capacity and Water Content An ion-exchange membrane was immersed in an aqueous solution containing 1 mol/l of HCl, for 10 hours or more.

Then, the ion-exchange membrane, when it was a cation-exchange membrane, was converted from a hydrogen ion type into a sodium ion type, using an aqueous solution containing 1 mol/l of NaCl. The hydrogen ion liberated was determined quantitatively (A mol) with an aqueous sodium hydroxide solution, using a potential-difference titration apparatus (COMTITE-900 produced by Hiranuma Sangyo K.K.).

Meanwhile, the ion-exchange membrane, when it was an anion-exchange membrane, was converted from a chloride ion type into a nitric acid ion type, using an aqueous solution containing 1 mol/l of $NaNO_3$. The chloride ion liberated was determined quantitatively (A mol) with an aqueous silver nitrate solution, using a potential-difference titration apparatus (COMTITE-900 produced by Hiranuma Sangyo K.K.).

Next, the same ion-exchange membrane was immersed in an aqueous solution containing 1 mol/l of HCl, for 4 hours or more, then thoroughly washed with an ion-exchanged water, and taken out. The membrane was wiped with a tissue paper or the like to remove the water present on the surface and then measured for the as-wet weight (W g). Then, the membrane was vacuum-dried at 60° C. for 5 hours and then measured for mass (D g). The ion-exchange capacity of the ion-exchange membrane used was calculated based on the above-obtained values, using the following expression.

Ion-exchange capacity=$A \times 1000/D$ (mmol/g-dry mass)

Water content=$100 \times (W-D)/D$ (%)

Fixed ion concentration=ion-exchange capacity/water content$\times 100$ (mmol/g-water)

(2) Membrane Resistance

There was prepared a two-chamber cell having therein two chambers separated by an ion-exchange membrane, wherein a platinum black electrode was placed in each chamber. An aqueous solution containing 3 mol/l of sulfuric acid was filled in each chamber present at both side of the ion-exchange membrane. The resistance between the two electrodes at 25° C. was measured using an AC bridge (frequency: 1,000 cycles/second) circuit. A difference between the resistance between the electrodes and the resistance between the electrodes when there was no ion-exchange membrane, was taken as membrane resistance. The membrane used in the above measurement was equilibrated beforehand in an aqueous solution containing 3 mol/l of sulfuric acid.
(3) Surface Roughness (Rz)

The surface roughness of the surface of an ion-exchange membrane was measured using a three-dimensional roughness tester (Model TDF-3A produced by Kosaka Kenkyusho). In the roughness curve obtained, a 10-point height of roughness profile (Rz) was employed with the evaluation length taken at 11 mm, and it was taken as the surface roughness of the ion-exchange membrane.

(4) Amount of Medicine Permeated in Virtial Skin System

Figure 2:
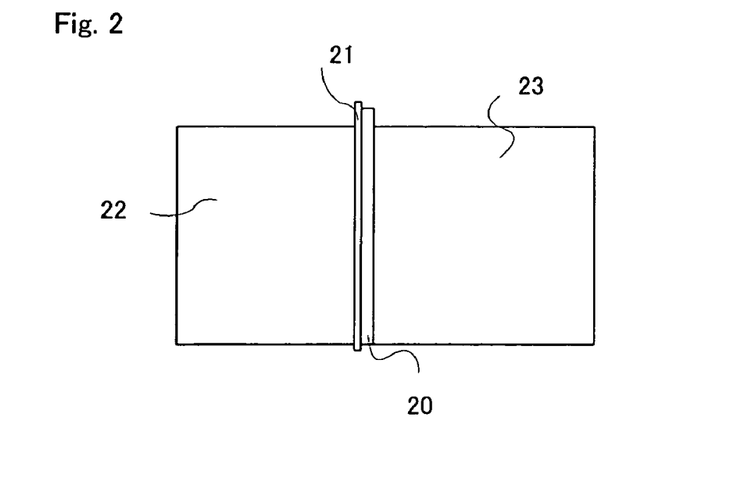
FIG. 2 is a schematic drawing of the apparatus used, in Examples, for measurement of permeation amount of medicine.

An aqueous solution containing 10% by mass of a polyvinyl alcohol (NH-20 produced by The Nippon Synthetic Chemical Industry Co., Ltd.) was coated on a filter paper (a chemical analysis filter paper 5C produced by Advantec). The amount of the solution coated was such that the amount of the polyvinyl alcohol after solvent removal was 2 mg/cm². Then, the filter paper was allowed to stand at room temperature for 24 hours or more to vaporize the water, whereby was obtained a virtual skin. Next, as shown in FIG. 2, the virtual skin 20 and a to-be-examined membrane (e.g. an ion-exchange membrane) 21 were placed in the center of a cell, with the skin and the membrane contacted tightly with each other. An aqueous solution containing a given concentration of a medicine was filled in a medicine solution chamber 22; and an aqueous solution containing 0.9% by mass of sodium chloride was filled in a virtual skin chamber 23. Then, a permeation test was conducted at 25° C. for a given period of time with the inside of the medicine solution chamber 22 and the inside of the virtual skin chamber 23 being stirred. Right after the completion of the test, the solution inside the virtual skin chamber 23 was withdrawn and used as a sample for measurement. The amount of medicine in the sample was determined using liquid chromatography.

(5) Amount of Medicine Permeated in Living Body Skin System

The amount of the medicine permeated was measured in the same manner as in the virtual skin system, by replacing the virtual skin (a filter paper coated with a polyvinyl alcohol) with a living body skin, i.e. the back skin of miniature pig (Yucatane Micropig, 5 month-old, female).

Production Example 1

There were prepared a monomer composition consisting of 380 g of chloromethylstyrene, 20 g of divinylbenzene and 20 g of tert-butyl peroxyethylhexanoate. 420 g of this monomer composition was placed in a 500-ml glass container. In the monomer composition was immersed a 20 cm×20 cm porous membrane (made of a polyethylene having a weight-average molecular weight of 250,000, membrane thickness=25 μm, average pore diameter=0.03 μm, void ratio=37%) at atmospheric pressure at 25° C. for 10 minutes, to impregnate the porous membrane with the monomer composition. Subsequently, the porous membrane was taken out of the monomer composition; the both sides of the membrane were covered with a polyester film of 100 μm in thickness; the covered membrane was sandwiched between two smooth stainless steel plates; and polymerization was conducted at 80° C. for 5 hours at a nitrogen pressure of 0.29 Mpa (3 kg/cm²). The resulting membrane-like material was immersed in an amination bath comprising 15% by mass of trimethylamine, 60% by mass of water and 25% by mass of acetone. A reaction was allowed to take place at room temperature for 5 hours to obtain an anion-exchange membrane of quaternary ammonium type.

The anion-exchange membrane obtained was measured for ion-exchange capacity, water content, fixed ion concentration, membrane resistance, membrane thickness and surface roughness. The results are shown in Table 1.

Production Examples 2 to 5

Anion-exchange membranes were produced in the same manner as in Production Example 1 except that there were used monomer compositions and porous membranes, all shown in Table 1. The properties of the membranes obtained are shown in Table 1.

Production Example 6

A monomer composition shown in Table 1 was impregnated into a porous membrane in the same manner as in Production Example 1. Subsequently, the porous membrane was taken out of the monomer composition. The both sides of the membrane were covered with a polyester film of 100 μm in thickness. The covered membrane was sandwiched between two stainless steel plates. Polymerization was conducted at 45° C. for 3 hours and then at 75° C. for 5 hours, at a nitrogen pressure of 0.29 Mpa (3 kg/cm²). The resulting membrane-like material was immersed in a 1:3 (mass ratio) mixed solution of methyl iodide and n-hexane at 30° C. for 24 hours to obtain an anion-exchange membrane of quaternary pyridinium type.

The anion-exchange membrane obtained was measured for ion-exchange capacity, water content, fixed ion concentration, membrane resistance, membrane thickness and surface roughness. The results are shown in Table 1

TABLE 1

| | | | | | | | | Properties of ion-exchange membrane | | | | |
|---|---|---|---|---|---|---|---|---|---|---|---|---|
| Production Examples | Porous film | Composition (mass ratio) | | | | | Ion-exchange group | Ion-exchange capacity (mmol/g-dry membrane) | Water content (%) | Fixed ion concentration (mmol/g-water) | Membrane resistance ($\Omega \cdot cm^2$) | Membrane thickness (μm) | Surface roughness (μm) |
| | | CMS | 4-VP | St | DVB | PO | | | | | | | |
| 1 | A | 95 | 0 | 0 | 5 | 5 | Quaternary ammonium type | 1.8 | 22 | 8.2 | 0.08 | 32 | 1 or less |
| 2 | A | 97.5 | 0 | 0 | 2.5 | 5 | Quaternary ammonium type | 2.0 | 35 | 5.7 | 0.07 | 32 | 1 or less |
| 3 | A | 80 | 0 | 0 | 20 | 5 | Quaternary ammonium type | 1.6 | 12 | 13.3 | 0.32 | 30 | 1 or less |
| 4 | B | 95 | 0 | 0 | 5 | 5 | Quaternary ammonium type | 1.9 | 24 | 7.9 | 0.06 | 20 | 1 or less |
| 5 | C | 95 | 0 | 0 | 5 | 5 | Quaternary ammonium type | 1.8 | 23 | 7.8 | 0.22 | 90 | 1 |

TABLE 1-continued

| Production Examples | Porous film | Composition (mass ratio) | | | | | Ion-exchange group | Ion-exchange capacity (mmol/g-dry membrane) | Water content (%) | Fixed ion concentration (mmol/g-water) | Membrane resistance ($\Omega \cdot cm^2$) | Membrane thickness ($\mu m$) | Surface roughness ($\mu m$) |
|---|---|---|---|---|---|---|---|---|---|---|---|---|---|
| | | CMS | 4-VP | St | DVB | PO | | | | | | | |
| 6 | A | 0 | 95 | 0 | 5 | 5 | Quaternary pyridinium type | 1.9 | 23 | 8.3 | 0.08 | 31 | 1 or less |
| 7 | A | 0 | 0 | 90 | 10 | 5 | Sulfonic acid type | 2.4 | 29 | 8.3 | 0.08 | 31 | 1 or less |
| 8 | A | 0 | 0 | 80 | 20 | 5 | Sulfonic acid type | 2.0 | 18 | 11.1 | 0.17 | 29 | 1 or less |
| 9 | A | 0 | 20 | 75 | 5 | 5 | Sulfonic acid type | 1.5 | 33 | 4.5 | 0.09 | 31 | 1 or less |
| 10 | A | 0 | 40 | 55 | 5 | 5 | Sulfonic acid type | 0.5 | 29 | 1.6 | 0.14 | 30 | 1 or less |
| 11 | A | 0 | 50 | 48 | 2 | 5 | Sulfonic acid type | 0.3 | 37 | 0.7 | 0.10 | 29 | 1 or less |
| Nafion 112 | Not used | | | | | | Sulfonic acid type | 1.0 | 21 | 4.8 | 0.11 | 45 | 1 or less |
| Neosepta AMX | Woven cloth | | | | | | Quaternary ammonium type | 1.5 | 25 | 6.0 | 0.35 | 150 | 11 |
| Neosepta CMX | Woven cloth | | | | | | Sulfonic acid type | 1.6 | 28 | 5.7 | 0.36 | 160 | 12 |

Porous film
A: Made of a polyethylene of 250,000 (weight-average molecular weight), film thickness = 25 $\mu m$, average pore diameter = 0.03 $\mu m$, void ratio = 37%
B: Made of a polyethylene of 200,000 (weight-average molecular weight), film thickness = 16 $\mu m$, average pore diameter = 0.03 $\mu m$, void ratio = 47%
C: Made of a polytetrafluoroethylene, film thickness = 80 $\mu m$, average pore diameter = 1 $\mu m$, void ratio = 80%
CMS: Chloromethylstyrene
4-VP: 4-Vinylpyridine
St: Styrene
DVB: Divinylbenzene
PO: t-butyl peroxyethylhexanoate Production Examples 7 to 11

A monomer composition shown in Table 1 was impregnated into a porous membrane in the same manner as in Production Example 1. Successively, the porous membrane was taken out of the monomer composition. The both sides of the membrane were covered with a polyester film of 100 $\mu m$ in thickness. The covered membrane was sandwiched between two stainless steel plates. Polymerization was conducted at 80° C. for 5 hours at a nitrogen pressure of 0.29 Mpa (3 kg/cm$^2$). The resulting membrane-like material was immersed in a 1:1 mixture of 98% concentrated sulfuric acid and chlorosulfonic acid (purity: 90% or more) to obtain cation-exchange membranes of sulfonic acid type.

The cation-exchange membranes obtained were measured for ion-exchange capacity, water content, fixed ion concentration, membrane resistance, membrane thickness and surface roughness. The results are shown in Table 1.

Examples 1 to 6

The amounts of medicine permeated in virtual skin system were measured using a solution containing 10 mmol/l of magnesium salt of ascorbic acid-phosphoric acid ester (an anionic medicine). The ion-exchange membranes used and the amounts of medicine permeated are shown in Table 2.

TABLE 2

| | To-be-examined ion-exchange membrane used | Medicine concentration (mmol/l) | Duration of permeation (hr) | Amount of permeation ($\mu mol/cm^2$) |
|---|---|---|---|---|
| Example 1 | Production Example 1 membrane | 10 | 1 | 2.5 |
| | | | 2 | 5.5 |
| | | | 3 | 10.2 |
| Example 2 | Production Example 2 membrane | 10 | 3 | 8.8 |
| Example 3 | Production Example 3 membrane | 10 | 3 | 6.0 |
| Example 4 | Production Example 4 membrane | 10 | 3 | 10.0 |
| Example 5 | Production Example 5 membrane | 10 | 3 | 8.0 |
| Example 6 | Production Example 6 membrane | 10 | 3 | 9.6 |
| Comparative Example 1 | Neosepta AMX | 10 | 1 | 0.5 |
| | | | 2 | 1.1 |
| | | | 3 | 1.8 |
| Comparative Example 2 | Not used | 10 | 1 | 0.6 |
| | | | 2 | 1.3 |
| | | | 3 | 2.0 |

Medicine used: magnesium salt of ascorbic acid-phosphoric acid ester

Comparative Example 1

The amount of medicine permeated was measured in the same manner as in Example 1 except that there was used Neosepta AMX (a product of TOKUYAMA CORPORATION) which was an anion-exchange membrane using a woven cloth as the base material (the properties of the membrane are shown in Table 1). The result is shown in Table 2.

Comparative Example 2

The amount of medicine permeated was measured in the same manner as in Example 1 except that no ion-exchange membrane was used and only a virtual skin was used. The result is shown in Table 2.

Example 7

The amount of medicine permeated in virtual skin system was measured for the membrane obtained in Production Example 1, using, in place of the solution containing 10 mmol/l of magnesium salt of ascorbic acid-phosphoric acid ester, a solution containing 10 mmol/l of sodium ascorbate. The result is shown in Table 3.

TABLE 3

| | To-be-examined ion-exchange membrane used | Medicine concentration (mmol/l) | Duration of permeation (hr) | Amount of permeation (µmol/cm²) |
|---|---|---|---|---|
| Example 7 | Production Example 1 membrane | 10 | 3 | 15.1 |
| Comparative Example 3 | Neosepta AMX | 10 | 3 | 4.5 |
| Comparative Example 4 | Not used | 10 | 3 | 5.2 |

Medicine used: Sodium ascorbate

Comparative Example 3

The amount of medicine permeated was measured in the same manner as in Example 7 except that there was used Neosepta AMX (a product of TOKUYAMA CORPORATION) which was an anion-exchange membrane using a woven cloth as the base material (the properties of the membrane are shown in Table 1). The result is shown in Table 3.

Comparative Example 4

The amount of medicine permeated was measured in the same manner as in Example 7 except that no to-be-examined ion-exchange membrane was used and only a virtual skin was used. The result is shown in Table 3.

Examples 8 to 13, Comparative Examples 5 and 6

The amounts of medicine permeated in virtual skin system were measured using a solution containing 10 mmol/l of histamine dihydrochloride (a cationic medicine). The ion-exchange membranes used and the amounts of medicine permeated are shown in Table 4.

Incidentally, Nafion 112 (a membrane produced by DuPont, its properties are shown in Table 1) used in Example 13 is a non-crosslinked cation-exchange membrane.

TABLE 4

| | To-be-examined ion-exchange membrane used | Medicine concentration (mmol/l) | Duration of permeation (hr) | Amount of permeation (µmol/cm²) |
|---|---|---|---|---|
| Example 8 | Production Example 7 membrane | 10 | 3 | 11.0 |
| Example 9 | Production Example 8 membrane | 10 | 3 | 10.0 |
| Example 10 | Production Example 9 membrane | 10 | 3 | 14.4 |
| Example 11 | Production Example 10 membrane | 10 | 3 | 10.7 |
| Example 12 | Production Example 11 membrane | 10 | 3 | 6.6 |
| Example 13 | Nafion 112 | 10 | 3 | 6.0 |
| Comparative Example 5 | Eeosepta CMX | 10 | 3 | 2.2 |
| Comparative Example 6 | Not used | 10 | 3 | 2.5 |

Medicine used: histamine dihydrochloride

Example 14, Comparative Examples 7 and 8

The amounts of medicine permeated in living body skin system were measured using a solution containing 10 mmol/l of sodium ascorbate (an anionic medicine). The ion-exchange membranes used and the amounts of medicine permeated are shown in Table 5.

TABLE 5

| | To-be-examined ion-exchange membrane used | Medicine concentration (mmol/l) | Duration of permeation (hr) | Amount of permeation (µmol/cm²) |
|---|---|---|---|---|
| Example 14 | Production Example 7 membrane | 10 | 1 | 0.10 |
| | | | 2 | 0.47 |
| | | | 3 | 0.88 |
| Comparative Example 7 | Neosepta AMX | 10 | 1 | 0.001 |
| | | | 2 | 0.002 |
| | | | 3 | 0.004 |
| Comparative Example 8 | Not used | 10 | 1 | 0.003 |
| | | | 2 | 0.005 |
| | | | 3 | 0.007 |

Medicine used: sodium ascorbate

Example 15, Comparative Example 9

The amounts of medicine permeated in living body skin system were measured using a solution containing 10 mmol/l of magnesium salt of ascorbic acid-phosphoric acid ester (an anionic medicine). The ion-exchange membranes used and the amounts of medicine permeated are shown in Table 6.

TABLE 6

| | To-be-examined ion-exchange membrane used | Medicine concentration (mmol/l) | Duration of permeation (hr) | Amount of permeation (µmol/cm²) |
|---|---|---|---|---|
| Example 15 | Production Example 7 membrane | 10 | 1 | 0.02 |
| | | | 2 | 0.10 |
| | | | 3 | 0.17 |

TABLE 6-continued

| To-be-examined ion-exchange membrane used | Medicine concentration (mmol/l) | Duration of permeation (hr) | Amount of permeation (μmol/cm$^2$) |
|---|---|---|---|
| Comparative Example 9 | Not used | 10 | 1 | 0.010 |
| | | | 2 | 0.013 |
| | | | 3 | 0.015 |

Medicine used: magnesium salt of ascorbic acid-phosphoric acid ester

The invention claimed is:

1. A patch for use in administration of an ionic medicine into a living body by infiltration of the ionic medicine into the living body through the living body surface without voltage application, wherein the patch is free of electrodes and comprises an ion-exchange membrane having a surface roughness (Rz) of 1 μm or less at its part to be brought into contact with the living body surface and an ionic medicine impregnated into the ion-exchange membrane.

2. The patch according to claim 1, wherein the ion-exchange membrane comprises a porous membrane made of a thermoplastic resin as the base material and an ion-exchange resin contained in voids of the base material.

3. The patch according to claim 2, wherein the ion-exchange resin is a crosslinked ion-exchange resin.

4. The patch according to claim 1, wherein an adhesive layer has been formed along the periphery of the part of the ion-exchange membrane to be brought into contact with the living body surface.

5. The patch according to claim 1, further comprising an ionic medicine-containing layer formed on the side of the ion-exchange membrane opposite to its side having the part to be brought into contact with the living body surface.

6. The patch according to claim 5, wherein the ion-exchange membrane comprises a porous membrane made of a thermoplastic resin as the base material and an ion-exchange resin contained in voids of the base material.

7. The patch according to claim 6, wherein the ion-exchange resin is a crosslinked ion-exchange resin.

8. The patch according to claim 5, wherein an adhesive layer has been formed along the periphery of the part of the ion-exchange membrane to be brought into contact with the living body surface.

9. A patch for use in administration of an ionic medicine into a living body, wherein the patch is free of electrodes, the patch consisting of an ion-exchange membrane having a surface roughness (Rz) of 1 μm or less at its part to be brought into contact with the living body surface, an ionic medicine-containing layer formed on the side of the ion-exchange membrane opposite to its side having the part to be brought into contact with the living body surface, an ionic medicine impregnated into the ion-exchange membrane and an ionic medicine-containing layer, a solvent-substantially-impermeable sheathing material and an adhesive layer for attachment of the patch material to the living body surface.

10. A method for administering an ionic medicine into a living body, comprising the steps of:
preparing a patch comprising an ion-exchange membrane having a surface roughness (Rz) of 1 μm or less at its part to be brought into contact with a living body surface and an ionic medicine impregnated into the ion-exchange membrane, wherein the patch is free of electrodes,
contacting the patch to the living body surface, and
allowing the medicine to infiltrate into the living body transdermally, without application of a voltage.

* * * * *